United States Patent [19]
Hasegawa et al.

[11] Patent Number: 5,609,740
[45] Date of Patent: Mar. 11, 1997

[54] CORROSION PREVENTIVENESS EVALUATION SYSTEM FOR COOLANT

[75] Inventors: Masatsune Hasegawa; Toshikazu Oya, both of Gifu; Takashi Hashimoto; Hironori Ezaki, both of Tokyo, all of Japan

[73] Assignee: CCI Co., Ltd., Gifu, Japan

[21] Appl. No.: 425,054

[22] Filed: Apr. 19, 1995

[30] Foreign Application Priority Data

Apr. 20, 1994 [JP] Japan ................................ 6-081751

[51] Int. Cl.$^6$ ............................................ G01N 27/26
[52] U.S. Cl. ................ 204/400; 204/290 R; 204/291; 204/292; 204/404; 204/435; 205/775; 205/775.5
[58] Field of Search ................................ 204/292, 400, 204/404, 435; 205/775, 775.5

[56] References Cited

U.S. PATENT DOCUMENTS

| | | | |
|---|---|---|---|
| 1,269,926 | 6/1918 | Gesell | 204/197 |
| 1,664,800 | 4/1928 | Mills | 204/197 |
| 2,310,561 | 2/1943 | Whitfield | 204/292 |
| 3,378,472 | 4/1968 | Banks et al. | 204/196 |
| 3,725,212 | 4/1973 | Kawamoto et al. | 205/775.5 |
| 4,147,596 | 4/1979 | Baboian et al. | 204/404 |
| 4,759,902 | 7/1988 | Anstine | 204/404 |

*Primary Examiner*—T. Tung
*Attorney, Agent, or Firm*—Thomas R. Vigil

[57] ABSTRACT

A system for evaluating the metal corrosion preventiveness of a coolant is disclosed, comprising a reference electrode (1), a working electrode (2) made of an iron material, preferably cast iron, and a voltage meter (3). The voltage meter is electrically connected with the reference electrode and the working electrode such that the redox potential to be generated between the two electrodes in the coolant (C) can be measured by the voltage meter when the two electrodes are partially submerged separately in the coolant. The system can provide an evaluation of the metal corrosion preventiveness of the coolant from the measurement of the redox potential. The cast iron for the working electrode may advantageously be surface-treated by tempering means or alkalization means.

5 Claims, 1 Drawing Sheet

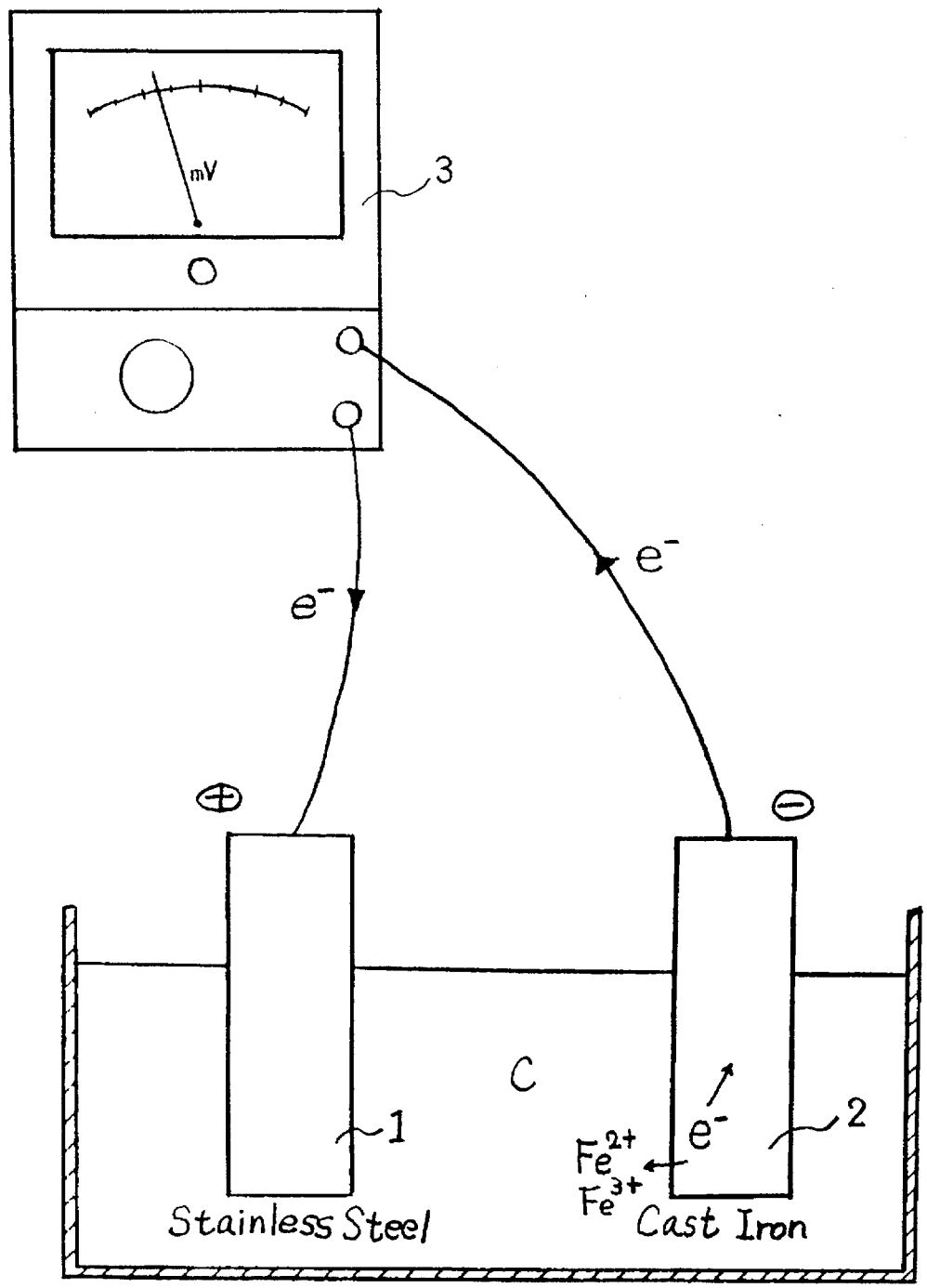
Fig 1 (Example)

CORROSION PREVENTIVENESS EVALUATION SYSTEM FOR COOLANT

BACKGROUND OF THE INVENTION

1. Field of the Invention

This invention generally relates to a system for evaluation of the metal corrosion preventiveness of coolants. More particularly, this invention relates to a system for "instantaneous" evaluation of the metal corrosion preventiveness of a coolant currently used generally in an internal-combustion engine system, providing an instant judgment whether it is proper or not to continuously use the coolant.

2. Description of the Prior Art

Generally, a coolant being used in an internal-combustion engine system includes a coolant composition available on the market and proportionally abundant diluting water. The coolant generally includes a metal corrosion preventive agent to provide the coolant with a metal corrosion preventive property for prevention of corrosion of the metal parts of the cooling system of the internal-combustion engine system.

The corrosion preventiveness of a coolant under use in an internal-combustion engine system, however, gets gradually deteriorated or degraded with time due mainly to the heat from the engine and occasional water supplement. The coolant with such degraded corrosion preventiveness will no longer provide adequate metal corrosion prevention and will eventually even promote corrosion of the metal portions of the cooling system of the internal-combustion engine system. In such a case, immediate change with a fresh coolant is recommended.

When the coolant in the cooling system of an internal-combustion engine system looks or is presumably judged no longer providing effective metal corrosion prevention or even promoting metal corrosion, it is generally time for the coolant to be wholly replaced with a fresh coolant containing a fresh corrosion preventive agent. Usually the time for such replacement is simply decided by the period of actual use of the coolant in a cooling system or by individual users' preferences, which naturally varies widely depending on individual users.

Such replacement or change of coolants in accordance with the duration of actual use of a coolant in an internal-combustion engine system or individuals' preferences is often inappropriate (inadequately late or unnecessarily soon) since the working condition of the coolant is subject to various factors of use of the engine system or the coolant. In addition, the time of such change is also subject to the components and/or quality of coolants as individual coolants can include different coolant compositions. Occasionally the coolant under use in a cooling system is changed with a fresh coolant too late and the corrosion of some metal parts in the cooling system may have already started. Occasionally the replacement of the coolant in a cooling system with a fresh coolant is unnecessarily too soon.

A coolant testing conventionally practiced for evaluation of the metal corrosion preventiveness of coolants after considerable use comprises an indirect evaluation of the metal corrosion preventiveness of coolants by studying the conditions of various elements of the coolants such as the concentration of the contained ethylene glycol, pH values and the concentration of various metal ions liberated in the coolants as well as the concentration of the other metal corrosion preventive agents.

Another coolant testing conventionally practiced for evaluation of the metal corrosion preventiveness of coolants after considerable use comprises a direct evaluation of the metal corrosion preventiveness of the coolants by directly studying the corrosion of various metal samples by submerging in the coolants under predetermined conditions.

Such an indirect evaluation of the corrosion preventiveness of coolants, however, will not always provide reliable judgment on the workability of the coolants tested due to the lack of reliable criteria for judgment. Without reliable criteria for judgment, it is not possible to precisely determine whether the coolant tested is proper or not to be continuously used. Further, the data obtained from such an indirect evaluation test fluctuate excessively depending on the constitution or components of coolants, making such judgment virtually impractical. In addition, each such measurement requires an extensive and expensive measurement system which can only be utilized in a research facility.

On the other hand, such a direct evaluation of the metal corrosion preventiveness of coolants also requires a special testing system which can only be used in a research facility, thus incapable of providing an instantaneous evaluation.

Neither of such testing methods can be easily or practically performed by individual users on the spot to determine whether the coolant in the cooling system of their cars, for instance, can be continuously used for some more time or should be replaced immediately before the metal portions of the cooling system start to get corroded.

Japanese Patent Publication No. 63-19815 (U.S. patent application 866074, Dec. 30, 1977, Assignee: Texas Instruments Incorporated) discloses a simple testing apparatus for coolant corrosion preventiveness. This apparatus comprises a silver reference electrode and a sensor or working electrode comprising steel and aluminum. The corrosion preventiveness of coolants is indirectly studied from the redox potential to be chemically generated between the two electrodes placed in the coolant tested.

The reliability of the above apparatus at first may be considerable, however, the reliability is destined to deteriorate with time and after repeated use of the electrodes of the apparatus as the electrodes themselves eventually get corroded, eventually providing metal corrosive evaluation data which are no longer reliable or off the true evaluation values. Because of this intrinsic defect, the above coolant evaluation apparatus will wrongly judge that a still usable coolant should be replaced immediately.

There has long been felt a need by users, mechanics and servicemen as well as dealers of coolant compositions or metal corrosion preventives for a reliable and handy as well as quick test system for evaluation of the metal corrosion preventiveness of coolants which can be used for a long duration of time without losing its reliability.

Accordingly, it is an object of the present invention to provide an evaluation test system for quickly, accurately and handily evaluating the metal corrosion preventiveness of coolants being used in cooling systems generally of internal-combustion engine systems.

It is another object of the present invention to provide an evaluation test system for reliably evaluating over a long duration of time the metal corrosion preventiveness of coolants being used generally in internal-combustion engine systems.

SUMMARY OF THE INVENTION

The coolant evaluation system for evaluation of the corrosion preventiveness of coolants (hereinafter sometimes referred to just as "evaluation system") of the present invention comprises a reference electrode, a sensor or working electrode electrically separated from the reference electrode, and a voltage meter electrically connected with both the electrodes to measure in voltage the redox potential to be generated between the two electrodes when the two electrodes are partially submerged in a coolant to be evaluated.

The expression "electrically separated" as used here includes that the reference electrode and the working electrode are to be physically separately arranged in a coolant, or that the reference electrode is to be placed as core inside the working electrode as sheath in a coolant without direct contact between the two electrodes.

The reference electrode is advantageously made of a metal material which hardly corrodes in water or coolant. The reference electrode may be a hydrogen electrode, platinum (black) electrode, calomel electrode, silver-silver chloride electrode, ferrous sulfate-mercury electrode, or mercury oxide electrode. Alternatively, the reference electrode can be a platinum-based electrode or silver-based electrode. Advantageously, the reference electrode is made of stainless steel, which is not only anticorrosive in coolant but also an economical material.

The working electrode is preferably made of an iron material such as pure iron, pig iron or cast iron. Steel is not appropriate to be made into the working electrode for the present invention. Cast iron is advantageously employed in the present invention, for cast iron is very sensitive to a metal corrosive environment.

The redox potential to be generated between the reference electrode and the working electrode in a coolant is subject to change in accordance with the degree of metal corrosiveness of the coolant. Therefore, when cast iron is made into the working electrode of the present invention, the working electrode can more advantageously and sensitively provide analysis or evaluation of the metal corrosion preventiveness of coolants than most other metal materials.

Pure iron, pig iron or cast iron may be used as the working electrode without any special treatment, however, it is advantageous to provide an oxidized layer on their surface or to provide an oxidation treatment onto their surface.

The oxidation treatment of their surface can be provided by conventional alkalization (blackening) means or tempering means. The alkalization means comprises submerging a cast iron electrode in a boiling high-concentration alkali solution. The surface of the cast iron electrode will be covered with an oxidized black layer of an iron oxide. On the other hand, the tempering means comprises heating a cast iron electrode in the air until the surface of the cast iron electrode is given a predetermined temperature or color. After an appropriate treatment of the heated cast iron electrode, the surface of the metal is provided with an oxidized layer of an iron monoxide or triiron tetraoxide (iron oxide, black) depending on the treatment condition.

When the reference electrode and the working electrode are partially placed in a coolant to be tested as shown in FIG. 1, redox potential is generated between the reference electrode and the working electrode. This phenomenon may be briefly explained as follows, using an example system comprising a working electrode made of cast iron and a reference electrode made of stainless steel both of which are to be partially submerged in the coolant (FIG. 1).

The following chemical reaction will take place in the coolant about the surface of the working cast iron electrode (coolants are generally "redox potential" inducing).

$$Fe \rightarrow Fe^{2+} + 2e^- \qquad (1)$$

Electrons are generated on the working electrode, which start to be attracted toward the reference stainless steel electrode via the voltage meter (as shown in FIG. 1).

Either of the following chemical reactions takes place in the coolant about the reference electrode depending on the pH value of the coolant.

$$1/2O_2 + H_2O + 2e^- \rightarrow 2OH^- \qquad (2)$$

(neutral pH value: oxygen consuming type)

$$2H^+ + 2e^- \rightarrow H_2\uparrow \qquad (3)$$

(acidic pH value: hydrogen generating type)

During either of such chemical reactions in the coolant tested, the working electrode functions as (chemical) anode and the reference electrode functions as (chemical) cathode.

A sensitive voltage meter connected to both the electrodes receives the subtle electric current generated between the two electrodes by the redox potential and may conveniently indicate the measurement in voltage (mV) after appropriate amplification by voltage amplifying means.

The redox potential to be generated between the two electrodes in the coolant tends to become (roughly correspondingly) higher as the metal corrosiveness of the tested coolant becomes higher. Therefore, it is possible to utilize the tendency to indirectly evaluate the metal corrosiveness or metal corrosion preventiveness of the coolant by studying or evaluating the generated redox potential.

The voltage meter may be advantageously and conveniently provided with a voltage amplifier to amplify the subtle redox potential values or voltage measured between the two electrodes. (Our evaluation test system incorporated such amplifying means.)

The voltage meter may also be advantageously and conveniently provided with judgment means which judges the usability of a coolant as regards its metal corrosion preventiveness, such as by flashing lights or buzzing when it judges the coolant to be no longer usable or to be replaced with a fresh coolant such that users of the evaluation system of the present invention can instantly and easily know the judgment.

BRIEF DESCRIPTION OF THE DRAWING

FIG. 1 schematically shows an example of the evaluation apparatus of the present invention where the reference electrode is indicated by numeral 1, the working electrode by numeral 2 and the voltage meter by numeral 3, while the coolant being tested is indicated by reference "C".

DETAILED DESCRIPTION OF THE PREFERRED EMBODIMENT

The present invention will be further explained hereunder in more detail. First, used coolants were studied conventionally in order to know which of them can be judged as "continuously usable" or "to be replaced". The judgment made conventionally was utilized for the evaluation system of the present invention, which is capable of indicating the overall evaluation in a single factor (advantageously "mV"), greatly simplifying the judgment making.

(1) Conventional Criterion Setting:

Used coolants taken from actually serving seven taxis as samples were studied by conventional means in order to utilize the obtained data in setting the evaluation criterion for the evaluation system of the present invention for evaluation of used coolants for their metal corrosion preventiveness. The concentration of ethylene glycol, pH values and concentration of various liberated metal ions in the sample coolants were respectively studied. Concurrently, metal corrosion tests according to "JIS K 2234-1987" were conducted on the sample coolants using various metal samples. Table I shows the results of the studies.

reference electrode 1 and the working electrode 2 both to be partially submerged in a coolant (C) are to be electrically connected with the voltage meter 3 which is to measure the redox electric potential to be generated between the electrodes 1 and 2 in the coolant (C) and to indicate the measurements in voltage, preferably in mV after certain

TABLE I

CRITERION SETTING TEST
(Conventional)

|  | SAMPLE NUMBER | | | | | | |
|---|---|---|---|---|---|---|---|
|  | 1 | 2 | 3 | 4 | 5 | 6 | 7 |
| DURATION (month) | 36 | 36 | 37 | 36 | 6 | 55 | 55 |
| DISTANCE (1000 km) | 16.9 | 20.2 | 18.3 | 19.2 | 18.7 | 26.4 | 28.3 |
| CONCENTRATION OF ETHYLENE GLYCOL (wt. %) | 31 | 33 | 18 | 23 | 18 | 6 | 6 |
| pH VALUE | 6.8 | 7.0 | 7.2 | *5.8 | *6.2 | *5.8 | *5.5 |
| ALUMINUM ION (ppm) | 1.1 | 0.9 | 0.6 | 0.0 | 0.0 | 0.0 | 0.0 |
| IRON ION (ppm) | 0.8 | 0.1 | 0.1 | 0.0 | 0.0 | *35.9 | *13.5 |
| COPPER ION (ppm) | 2.5 | 5.7 | 5.3 | *22 | 5.0 | 0.1 | 0.0 |
| WEIGHT CHANGE (LOSS) (mg/cm$^2$) | | | | | | | |
| CAST ALUMINUM | −0.01 | −0.01 | −0.01 | −0.10 | *−0.48 | *−2.89 | *−1.21 |
| CAST IRON | 0.09 | 0.01 | 0.06 | *−0.32 | *−13.6 | *−167.0 | *−179.5 |
| STEEL | 0.01 | −0.03 | 0.01 | *−0.41 | *−2.45 | *−21.73 | *−19.36 |
| BRASS | −0.10 | −0.05 | −0.04 | −0.03 | −0.02 | *−0.81 | *−1.07 |
| SOLDER | −0.02 | 0.11 | 0.00 | −0.10 | *−0.22 | *−27.10 | *−19.18 |
| COPPER | −0.06 | −0.04 | −0.08 | −0.03 | −0.03 | *−0.33 | *−0.65 |
| JUDGMENT | US | US | US | UN | UN | UN | UN |

In Table I, "US" indicates "usable" or "can be continuously used" and "UN" indicates "unusable" or "improper to be continuously used", while the mark "*" indicates "abnormal" values, given in accordance with our criterion. Those abnormal values suggest that the coolants with such evaluation are not suitable for continuous use.

Our foregoing studies have enabled us to set the judgment criterion for evaluation of coolants to distinguish between "usable" and "unusable" of the coolants as regards their metal corrosiveness. According to the criterion we have set for the present invention, the "usable" includes pH value 6.5–11 and metal ion concentrations 10 ppm or less.

The "usable" also includes the range of weight gains or losses per unit area (mg/cm$^2$) in the metal corrosion tests for cast aluminum within ±0.3, cast iron within ±0.3, steel within ±0.15, brass within ±0.15, solder within ±0.15 and copper within ±0.15. These metals are ones commonly used in the cooling system of an interenal-combustion engine system.

Then, evaluation tests in an attempt to set the evaluation criterion for the present invention were conducted using the test apparatus set as shown in FIG. 1 as an example. The evaluation criterion we set was to prove the feasibility and practicability of our invention.

(2) Criterion Setting for the Present Invention:

The evaluation test apparatus shown in FIG. 1 (example) was used to set the criterion for the judgment of coolants regarding their metal corrosion preventiveness utilizing the criterion previously set in accordance with the foregoing conventional tests.

An example evaluation system of the present invention comprises a stainless steel reference electrode 1, a cast iron working electrode 2 and a voltage meter 3 (FIG. 1). The amplification. The stainless steel used for the reference electrode 1 may advantageously be an "SUS-304" type.

In order to discover suitable materials for the working electrode 2, a plurality of working electrode samples 2 were prepared, respectively, of cast iron, corroded cast iron (prepared by submerging cast iron in a JIS preparatory solution and drying same), black or blackened cast iron (prepared by an alkalization treatment of the surface), tempered cast iron (prepared by tempering cast iron), steel, aluminum, zinc, copper-plated iron, zinc-plated iron, and aluminum-steel. These electrodes 2 were independently partialy submerged in coolants (C) each together with the foregoing reference electrode 1 as shown in FIG. 1.

The coolants used for these studies had been conventionally tested for corrosion preventiveness as described earlier so that the "usability" or "unusability" of the coolants had been already known or judged in accordance with their behaviors. Bipolar electrodes prepared of aluminum and steel in accordance with Japanese Patent Publication No. 63-19815 were also tested under the identical condition for comparison.

Following Table II shows the measurements taken from these tests in mV after certain amplification. The judgments made in accordance with the previous conventional studies are also given in Table II and indicated by "US" for "usable" or "UN" for "unusable".

TABLE II

CRITERION SETTING TEST
(Present Invention)

COOLANT SAMPLE NUMBER

|  | 1 | 2 | 3 | 4 | 5 | 6 | 7 |
|---|---|---|---|---|---|---|---|
| JUDGMENT | US | US | US | UN | UN | UN | UN |
| CAST IRON | 0 | 80 | 30 | 300 | 360 | 470 | 590 |
| CORRODED CAST (N 1) | 30 | 110 | 180 | 320 | 400 | 520 | 630 |
| CORRODED CAST (N 2) | 0 | 60 | 150 | 250 | 270 | 430 | 500 |
| CORRODED CAST (N 3) | 0 | 70 | 50 | 280 | 330 | 450 | 570 |
| BLACK CAST (N 1) | 0 | 60 | 10 | 280 | 320 | 450 | 540 |
| BLACK CAST (N 2) | 0 | 70 | 20 | 260 | 340 | 430 | 570 |
| BLACK CAST (N 3) | 0 | 60 | 10 | 270 | 320 | 440 | 560 |
| TEMPERED CAST (N 1) | 0 | 40 | 0 | 230 | 290 | 420 | 510 |
| TEMPERED CAST (N 2) | 0 | 50 | 0 | 240 | 280 | 410 | 520 |
| STEEL | 210 | 150 | 120 | 230 | 180 | 410 | 460 |
| ALUMINUM | 410 | 510 | 430 | 470 | 310 | 250 | 320 |
| ZINC | 900 | 860 | 880 | 780 | 820 | 1300 | 1100 |
| COPPER-PLATED | 560 | 680 | 860 | 450 | 680 | 460 | 620 |
| ZINC-PLATED | 1100 | 680 | 720 | 590 | 680 | 1100 | 1200 |
| AlUMINUM/STEEL | 450 | 530 | 360 | 430 | 360 | 480 | 520 |

The values are given all in mV (after amplification).

Description of the Used Electrodes:
  (a) The size of all electrodes used was 10 mm×10 mm.
  (b) The cast iron, steel, aluminum and zinc electrodes were ground with #800 water resistive grind paper and were washed thereafter in ethanol using ultrasonic means, and then dried.
  (c) The corroded cast iron electrodes were made from cast iron electrodes by submerging in a JIS preparatory solution for 1 week (N 1), 2 weeks (N 2) and 3 weeks (N 3), respectively, and drying.
  (d) The black cast iron electrodes were prepared by means of surface alkalization of cast iron electrodes to provide the surface with an oxidized layer (submerging in an alkali solution for 2 min. (N 1), 10 min. (N 2), and 20 min. (N 3), respectively, washing with ethanol and then drying).
  (e) The tempered cast iron electrodes were prepared by means of tempering cast iron electrodes, providing the surface with an oxidized layer (heating respectively for 5 min. (N 1) and 10 min. (N 2), washing with ethanol and then drying).

The judgment criterion we have set after these tests is as follows. It is important to note that this criterion provides only an example for the purpose of describing the present invention.

TABLE III

CRITERION FOR EVALUATION OF COOLANT

| | REMARKS |
|---|---|
| 0–150 mV | Sufficiently Corrosion Preventive Continuously Usable |
| 150–420 mV | Poorly Corrosion Preventive Change is Recommended |
| Over 420 mV | Very Poorly Corrosion Preventive Immediate Change is Needed |

The criterion above is given as an example for one embodiment of the present invention to describe how the evaluation system according to the present invention can be actually utilized, in which the redox potential generated between the two electrodes is to be conveniently amplified.

As described earlier, the redox potential generated between the reference electrode 1 and the working electrode 2 generally shows a tendency of becoming higher as the coolants increase their metal corrosiveness. From Table II, it can be seen that only untreated cast iron electrodes, black cast iron electrodes and tempered cast iron electrodes showed this tendency clearly. Steel electrodes, aluminum electrodes or zinc electrodes did not show this tendency clearly. Copper-plated iron electrodes or zinc-plated iron electrodes would not become advantageous working electrodes 2 to be used for the present invention since the surface materials (zinc and copper) of those plated metals alone count and are to be related to the redox potential.

Accordingly, it is suggested that the working electrodes 2 for the present invention can be prepared of untreated cast iron or treated cast iron such as black cast iron or tempered cast iron.

However, untreated cast iron itself is very susceptible to corrosion in coolant. Therefore, untreated cast iron electrodes will eventually provide misleading data in such a coolant evaluation test and will judge that still usable coolants be improper to be continuously used or "unusable".

Wet tests were conducted to study corrosivity of cast iron electrodes, black cast iron electrodes and tempered cast iron electrodes. Following Table IV shows the high corrosiveness of untreated cast iron electrodes and the low corrosiveness of surface-oxidized cast iron electrodes.

TABLE IV

RESULT OF WET TEST

| TESTED | APPEARANCE | | | | CHANGE IN WEIGHT |
|---|---|---|---|---|---|
| HOURS | 24 | 72 | 168 | 336 | (mg/cm²) |
| CAST IRON N 1 | Normal | Partly Corroded | Partly Corroded | Wholly Corroded | −0.46 |
| CAST IRON N 2 | Normal | Partly Corroded | Wholly Corroded | Wholly Corroded | −0.51 |
| BLACK CAST N 1 | Normal | Normal | Normal | Normal | −0.07 |
| BLACK CAST N 2 | Normal | Normal | Normal | Normal | −0.06 |
| TEMPERED CAST N 1 | Normal | Normal | Normal | Normal | −0.11 |
| TEMPERED CAST N 2 | Normal | Normal | Normal | Normal | −0.09 |

Wet Test Conditions:
  (a) Test pieces (FC-20 prepared in accordance with JIS K 2234 LLC) were respectively kept suspended in 300 ml tall beakers without touching the 50 ml pure water put in the beakers.
  (b) Heated air (50° C.) was constantly sent into the beakers to promote oxidation.
  (c) The weights of the cast iron test pieces treated in accordance with JIS K 2234 were measured after each 24 hrs., 72 hrs., 168 hrs., and 336 hrs, and respectively compared with their original weights.

(d) The changes in appearance of the test pieces were also observed and described in Table IV.

Tables IV clearly shows that untreated cast iron electrodes easily get corroded in coolant and lose weight, while surface-treated cast iron (black cast iron and tempered cast iron) hardly get corroded in coolant. As Table II shows, corroded cast iron electrodes will provide misleading data. Therefore, it can be concluded that cast iron electrodes having oxidized surface make advantageous working electrodes for the coolant evaluation system of the present invention.

Field of Utilization of the Invention:

The evaluation system of the present invention for evaluation of metal corrosion preventiveness of coolants can provide analysis and evaluation of a working coolant being used in an internal-combustion engine system for its effective metal corrosion preventiveness on the spot, very handily and accurately, and provide the user with an instant "judgment" which advises him or her to "continuously use", "onsider change" or change the coolant in his or her cooling system.

Therefore, the user can most economically use the coolant in his or her cooling system while preventing the corrosion of the metal portions of the cooling system, saving the trouble of unnecessarily changing or wasting the coolant as well.

Accordingly, general users such as drivers, mechanics, servicemen and dealers of coolant compositions or metal corrosion preventives can be advised at the most appropriate time to change coolants in the cooling systems of internal-combustion engine systems, preventing corrosion of the metal portions of the cooling systems or preventing wasting coolants.

The present invention has been described above. Various details of the present invention may be changed or altered without departing from its scope. Furthermore, the foregoing description of the preferred embodiment of the present invention is provided for the purpose of illustration only and not for the purpose of limiting the invention. The present invention is to be limited only by the appended claims.

What is claimed is:

1. A system for evaluating the metal corrosion preventiveness of a coolant, comprising a stainless steel reference electrode, a working electrode made of cast iron and a voltage meter electrically connected with said reference electrode and said working electrode such that the electric potential generated between said reference electrode and said working electrode can be measured, said reference electrode and said working electrode to be partially and separately submerged in said coolant and the redox potential generated between said reference electrode and said working electrode to be measured by said voltage meter.

2. The system of claim 1, wherein a surface of said cast iron electrode has been surface-treated by alkalization means to provide an oxidized layer on said surface.

3. The system of claim 1, wherein a surface of said cast iron electrode has been surface-treated by tempering means to provide an oxidized layer on said surface.

4. The system of claim 3, wherein said oxidized layer is ferrous oxide.

5. The system of claim 3, wherein said oxidized layer is ferriferrous oxide.

* * * * *

UNITED STATES PATENT AND TRADEMARK OFFICE
CERTIFICATE OF CORRECTION

PATENT NO. : 5,609,740
DATED : 3/11/97
INVENTOR(S) : Masatsune Hasegawa et al.

It is certified that error appears in the above-indentified patent and that said Letters Patent is hereby corrected as shown below:

On the title page, item
"[73] Assignee: CCL Co., Ltd., Gifu, Japan" should be --[73] Assignee: CCI Co., Ltd., Gifu, Japan and Hino Motors, Inc., Tokyo, Japan--

Signed and Sealed this

Third Day of March, 1998

*Attest:*

BRUCE LEHMAN

*Attesting Officer*       *Commissioner of Patents and Trademarks*